United States Patent [19]
Weitschies et al.

[11] Patent Number: 6,027,946
[45] Date of Patent: Feb. 22, 2000

[54] PROCESS AND COMPOUNDS FOR THE MAGNETORELAXOMETRIC DETECTION OF ANALYTES AND USE THEREOF

[75] Inventors: Werner Weitschies; Roman Kotitz; Lutz Trahms; Thomas Bunte, all of Berlin, Germany

[73] Assignee: Schering AG, Germany

[21] Appl. No.: 08/875,418

[22] PCT Filed: Jan. 29, 1996

[86] PCT No.: PCT/EP96/00339

§ 371 Date: Feb. 23, 1998

§ 102(e) Date: Feb. 23, 1998

[87] PCT Pub. No.: WO96/23227

PCT Pub. Date: Aug. 1, 1996

[30] Foreign Application Priority Data

Jan. 27, 1995 [DE] Germany .......................... 195 03 664

[51] Int. Cl.⁷ ........................ G01N 25/18; G01N 33/566; G01N 33/553
[52] U.S. Cl. .......................... 436/526; 436/501; 436/149; 436/173; 436/806; 435/7.1

[58] Field of Search ...................... 436/501, 512, 436/518, 523, 526, 525, 519, 517, 529, 63, 84, 86, 149, 173, 806; 435/7.1, 7.2; 324/248; 600/409

[56] References Cited

U.S. PATENT DOCUMENTS 5,164,297  11/1992  Josephson et al. .................... 435/7.25

FOREIGN PATENT DOCUMENTS 4309333    9/1994  Germany .
WO 91/15243  10/1991  WIPO .

*Primary Examiner*—Keith D. MacMillan
*Assistant Examiner*—P. Ponnaluri
*Attorney, Agent, or Firm*—Millen, White, Zelano & Branigan, P.C.

[57] ABSTRACT

The invention relates to a process for magnetorelaxometric quantitative detection of analytes in liquid and solid phases, compounds for magnetorelaxometric detection, and their use in analysis and immunomagnetography.

23 Claims, 4 Drawing Sheets

PROCESS AND COMPOUNDS FOR THE MAGNETORELAXOMETRIC DETECTION OF ANALYTES AND USE THEREOF

This application is a 371 of PCT/EP 96/00339 filed Jan. 29, 1996.

BACKGROUND OF THE INVENTION

The invention relates to processes for magnetorelaxometric qualitative and/or quantitative detection of analytes in liquid and solid phases, compounds for magnetorelaxometric detection, and their use in analysis and immunomagnetography.

It is known that immunoscintigraphy makes it possible to detect pathological structures in vivo with the aid of radiolabeled structure-specific substances, which are also referred to below as markers. To this end, antibodies that are labeled with γ-rays or antibody fragments are usually used. In addition, other structure-specific substances, such as, e.g., peptides or oligonucleic or polynucleic acids are also used or are being researched. The portion of specifically bound radioactivity is, however, generally small in all these processes. Consequently, in the case of these studies, the level of markers that are not specifically bound and thus circulate in the blood or accumulate in organs such as the liver, kidney, efferent urinary passages, or bladder is very high. In many cases, this high background radiation impedes adequate detection of pathological structures. Panchapakesan [Immunol. Cell Biol., 70 (1992) 295] and Ziegler [New England Journal of Medicine, 324 (1991) 430] therefore refer to ways of improving immunoscintigraphy. Such ways are also described in EP 0 251 494. The goal of most of the processes is to accelerate the elimination of radioactivity that is not specifically bound.

In addition, the use of antibodies that are conjugated with paramagnetic or superparamagnetic substances or antibody fragments for locating pathological structures in vivo has been proposed on various occasions. To date, nuclear spin tomography or magnetometry that is based on changes in susceptibility (WO 93/05818 and WO 91/15243) have been considered as detection processes for such labeled antibodies. In the case of these detection processes, the problem of the variable portion of the signal owing to unbound portions of the marker as well as owing to natural variations in the susceptibility and relaxivity of the tissue also remains present. In addition, the methods often are not sensitive enough to be able to detect just small amounts of specifically bound markers.

A process that makes it possible to detect only the portion of bound markers and thus is not influenced by the extent of the unbound markers is not known, however.

It is also known that quantitative immunoassays as well as other binding assays (e.g., receptor binding assays) make it possible to determine a very large number of substances that can also be of biological relevance in samples of varying composition. Generally, however, only one parameter per sample in an assay is determined in this way. An existing survey of the various processes is: T. Chard [An Introduction to Radioimmunoassay and Related Techniques: Laboratory Techniques in Biochemistry and Molecular Biology, 4th ed., Elsevier Science Publishers, Amsterdam (1990)]. The basis of all binding assays is the high detection sensitivity of compounds that are labeled with isotopes or by some other means with the high specificity of ligand-receptor reactions.

The known assay processes have the following drawbacks, however:

The processes for simultaneous determination of various analytes within the same sample are based on the binding of various radio-, fluorescence- or enzymologically-labeled probes to the analytes. In this case, the unbound or bound activity of the probes for quantitative determination of the analyte is generally measured after subsequent separation and washing. In this case, the amount of usable different probe labels is greatly limited. Thus, for example, in the case of different radioisotopes as probe labels, so-called overlapping phenomena occur which lead to a rapid loss of the quantitative accuracy of individual signals. The combination of various enzymes as probe labels causes comparable problems, whereby the feasibility here is further hampered by the necessary search for reaction conditions that allow the simultaneous determination of enzyme reactions in a system.

The sensitivity of the process is limited by, for example, non-specific interactions between matrix and probe, or else by limited labeling capability on the part of the probe (low specific activity).

The successful implementation of the process often requires that the sample material obtained be worked up (e.g., production of serum or plasma from whole blood, extraction of samples with organic solvents, concentration of the analyte using chromatographic processes, etc.).

For successful implementation of the processes, separation and washing steps, which are used in the separation of bound and unbound receptors or ligands, are essential in most cases.

To carry out radioimmunoassays, the use of radiating nuclides, which are costly and complicated to handle, is necessary.

In practice, the storage of previously used markers often causes problems since they are either unstable (radioimmunoassays) and must therefore constantly be made up fresh or else react in a sensitive manner to environmental influences.

SUMMARY OF THE INVENTION

The object of this invention was therefore to develop new processes and substances that overcome the drawbacks of the prior art and that especially are able to detect the retention site without using radioactive substances and the extent of the bound markers without prior separation of the unbound marker.

This object is achieved by this invention.

It has been found that the qualitative and/or quantitative detection of analytes in liquid and/or solid phases is possible if ferromagnetic or ferrimagnetic colloidal particles are used as magnetic labeling that is to be identified in immunoassays or other binding assays, and the relaxation of their magnetization is determined as a measurement variable.

Below, processes are first described that overcome the drawbacks of the known processes for implementing immunoassays or other binding assays.

The processes according to the invention are based on the use of colloidal ferromagnetic or ferrimagnetic substances, also referred to below as magnetic labeling, which are combined with substances that are to be identified—also referred to below as analytes—or structure-specific substances. Such combinations, according to the invention, of magnetic labelings with analytes or structure-specific substances, which are described in more detail in this patent, are also referred to below as magnetic markers. Through the use of the term colloidal substances or colloidal particles, both the range of sizes of the particles or substances in the size range of colloids, i.e., the range of 1 nm up to about 1000 nm, and their use as a dispersed phase in a suitable dispersion medium, which is aqueous in most cases, are described. To ensure improved storability and transportability, the colloidal substances or particles can also be present in dried form or frozen; while measurements are being made, however, they are present in the liquid phase in the dispersed state.

In addition, the processes are based on special measuring techniques, which make it possible to determine the relaxation of magnetization after the magnetic labeling or the magnetic markers are magnetized. Such measuring processes according to the invention, which are described in more detail in this patent, are also referred to below as magnet-relaxometry or magnetorelaxometry or magnet-relaxometric detection.

An important principle of the invention is that after an external magnetizing field is turned off, the magnetization of freely movable ferromagnetic or ferrimagnetic colloidal particles relaxes within the measuring time by two different mechanisms:

i) Turning of the whole colloidal particle inside the surrounding liquid, whereby the time constant depends on the hydrodynamic diameter of the particles including the shell, the viscosity of the carrier liquid, and temperature, which mainly reflects parameters of the environs of the particles; this mechanism is also referred to below as Brownian relaxation or extrinsic superparamagnetism, and ii) Turning of the internal magnetizing vector inside the colloidal particles, whereby the time constant depends in a very sensitive manner on material and shape (the anisotropy constants of the particle material used), volume and the temperature of the particles used. These are basically intrinsic parameters of the particles; this mechanism is also referred to below as Néelian relaxation or intrinsic superparamagnetism.

The object according to the invention is achieved by virtue of the fact that in immunoassays or other binding assays, ferromagnetic or ferrimagnetic colloidal particles, whose Brownian relaxation proceeds faster than the Néelian relaxation under measurement conditions in the unbound state, are used as magnetic labeling that is to be identified. Owing to the change in the predominant relaxation mechanism or to the scaling-up of the particle volume, which is caused by the binding, the use of such ferromagnetic or ferrimagnetic colloidal particles then makes it possible to determine specifically the portion of bound magnetic markers in addition to the unbound magnetic markers that are simultaneously present in the measuring sample.

By the use of sensitive measuring processes, in the case of the procedure according to the invention, ultrahighly sensitive binding-specific immunoassays or other binding assays which can be performed both in the liquid phase and in the solid phase can be set up using ferromagnetic or ferrimagnetic colloidal particles. As an especially sensitive measuring process, after the sample is magnetized in a magnetizing field and after the field is turned off, the relaxation of the magnetization can be determined with the aid of highly sensitive magnetic field detectors (such as, e.g., superconducting quantum interference devices (SQUIDs), induction coils, flux gate magnetometers, giant magnetoresistance sensors, or magnetoresistive converters), or the complex susceptibility of the sample can be determined as a function of frequency of the magnetizing field.

In addition, in the process for magnet-relaxometric quantitative detection of analytes in liquid and solid phases according to the invention, the structure-specific substances that bind the analytes first are labeled with ferrimagnetic or ferromagnetic colloidal particles.

These magnetically labeled structure-specific substances are used in a liquid or immobilized sample that is to be measured, and the sample that is to be measured is magnetized with the aid of a magnetic field that is applied from the outside. After the outside field is turned off, the relaxation of the magnetization of the magnetic markers is measured with the aid of magnetic field sensors.

The evaluation of the measuring results is made here, as also in the direct assay processes that are described below, according to methods known to one skilled in the art.

The process for magnet-relaxometric quantitative detection of analytes in liquid and solid phases according to the invention can also be carried out in such a way that analytes first i) are labeled with ferrimagnetic or ferromagnetic colloidal particles and then ii) these magnetically labeled analytes are used in a liquid or immobilized sample that is to be measured, the substances that specifically bind the analytes are added, and the sample that is to be measured is magnetized with the aid of a magnetic field that is applied from the outside and, after the outside field is turned off, the relaxation of the magnetization of the magnetic markers is measured with the aid of magnetic field sensors.

The evaluation of the measuring results is made here, as also in the competitive assay processes that are described below, in the way known to one skilled in the art, i.e., analogously to the processes as they are used in immunoassays or radioassays.

In both above-named cases, the measurement of the complex susceptibility of the magnetic labeling or the magnetic marker that is altered by the binding can also be used as a function of frequency for analysis.

The discrimination between bound and unbound markers, which previously could be done only in exceptional cases, is made possible by the use of their different relaxation mechanisms or the influence of the relaxation time of the magnetic marker that is caused by the binding.

Solid-phase-bound analytes can be identified according to the invention especially by the structure-specific substances that bind the analytes first i) being labeled with the ferrimagnetic or ferromagnetic colloidal particles that relax in the time range of the measurement, whereby the ferrimagnetic or ferromagnetic colloidal particles are selected in such a way that under the measurement conditions, the Brownian relaxation has a shorter relaxation time than the Néelian relaxation and then ii) these magnetically labeled substances being used in an immobilized sample that is to be measured, and the sample that is to be measured being magnetized with the aid of a magnetic field of suitable intensity that is applied from the outside and, after the outside field is turned off, the relaxation of the magnetization of the magnetic markers being measured with the aid of magnetic field sensors, whereby the different relaxation behaviors of solid-phase-bound and unbound magnetic markers are used for analysis. As a measurement variable, the complex susceptibility of the samples can also be determined as a function of frequency.

Also in this case, it is possible to combine the analytes that are to be identified, instead of structure-specific substances, with the magnetic labelings.

In the liquid phase, analytes according to the invention can be detected especially by the structure-specific substances that bind the analytes first i) being labeled with ferrimagnetic or ferromagnetic colloidal particles, whereby the ferrimagnetic or ferromagnetic colloidal particles are selected in such a way that under the measurement conditions the Brownian relaxation has a shorter relaxation time than the Néelian relaxation and then ii) these magnetically labeled substances being used in a sample that is to be measured, and the sample that is to be measured being magnetized with the aid of a magnetic field of suitable intensity that is applied from outside and, after the outside field is turned off, the relaxation of the magnetization of the magnetic markers being measured with the aid of magnetic field sensors, whereby the different relaxation behaviors of the magnetic markers bound with the analyte relative to the unbound magnetic markers are used for analysis.

As a measurement variable, the complex susceptibility of the samples can also be determined as a function of frequency.

Also in this case, it is possible to combine the analytes that are to be identified, instead of structure-specific substances, with the magnetic labelings.

Structure-specific substances are defined as all substances that bind specifically to certain structures. Structure-specific substances are defined as especially antibodies, antibody fragments, biotin, or substances that bind biotin such as avidin and streptavidin, agonists that bind specifically to receptors, such as cytokines, lymphokines, endothelins or their antagonists, specific peptides and proteins, receptors, enzymes, enzyme substrates, nucleotides, ribonucleic acids, deoxyribonucleic acids, carbohydrates, lipoproteins, etc. As structure-specific substances, substances are preferred whose binding constant is in the range of $10^5$–$10^{15}$ $(mol/l)^{-1}$. Especially preferred are substances whose binding constant is in the range of $10^7$–$10^{15}$ $(mol/l)^{-1}$.

The structure-specific substances or analytes that are to be identified can be labeled with the ferrimagnetic or ferromagnetic particles with the aid of processes that are familiar in immunochemistry, peptide chemistry, and protein chemistry. Especially advantageous are covalent bonds between the structure-specific substances or the analytes that are to be identified with the substances that form the stabilizing shell of ferrimagnetic or ferromagnetic particles. Examples of especially suitable methods are activation and coupling with the aid of carbodiimides [Jakoby and Wilchek, eds.; Methods Enzymol. (1974) 34], the formation of Schiff bases after periodates are exposed to compounds that contain carbohydrates (Wichek and Bayer, eds., Methods Enzym. 184:177), which are then optionally reduced for further stabilization, coupling with the aid of glutaric dialdehyde [Heitzmann and Richards, Proc. Natl. Acad. Sci. USA 71 (1974) 3537], cross-linking of bromoacetylated particles with thiolylated substances [Angerer et al.; Cell 9 (1976) 81], as well as reductive alkylation (Bayer et al.: J. Histochem. Cytochem. 24 (1976) 933].

Ferromagnetic or ferrimagnetic colloidal particles can also be produced with a stabilizing shell made of the structure-specific substance or the analyte that is to be identified, by the particles being put after production directly into a solution of the structure-specific substance, optionally in the presence of other adjuvants, such as, e.g., proteins, carbohydrates, as well as natural, synthetic, or partially synthetic surface-active substances, etc., or by being produced directly in the presence of structure-specific substances.

Suitable colloidal particles and suspensions that contain these particles are described in, for example, WO 92/12735, WO/92/22586, EP 0 186 616 and U.S. Pat. No. 4,101,435.

The process according to the invention can be used in, e.g., fertility, histocompatibility, allergology, infectiology, hygiene, genetics, virology, bacteriology, toxicology, pathology, environmental analysis, and medical diagnosis.

Another object of this invention are compounds for magnet-relaxometric detection, which consist of colloidal suspensions of freely movable ferrimagnetic or ferromagnetic particles and structure-specific substances or analytes that are to be identified, whereby structure-specific substances are defined as especially antibodies, antibody fragments, biotin, or substances that bind biotin such as avidin and streptavidin, agonists that bind specifically to receptors, such as cytokines, lymphokines, endothelins or their antagonists, other specific peptides and proteins, receptors, enzymes, enzyme substrates, nucleotides, ribonucleic acids, deoxyribonucleic acids, carbohydrates, lipoproteins, etc.

The compounds for magnet-relaxometric detection can also consist of combinations of several ferromagnetic or ferrimagnetic particles with relaxation times that can be discriminated, since measurement results that can be discriminated individually can be achieved through the use of different magnetic labelings with respectively a very narrow distribution of relaxation times and/or magnetic moments for various structure-specific substances or analytes inside a sample. As a result, direct simultaneous quantitative determination of several analytes is made possible.

As suspension media, all liquids in which the colloidal particles can move freely are suitable. Especially suitable are water, aqueous solutions of surface-active adjuvants, such as, e.g., surfactants or oligomeric or polymeric-carbohydrates and proteins, as well as mixtures of water with alcohols, such as, e.g., glycerol and polyethylene glycol. The suspension media can additionally contain adjuvants that change the osmotic pressure, such as, e.g., common salt. In addition, buffer substances that determine pH, such as, e.g., phosphates, can be contained.

The compounds that are made of ferromagnetic or ferrimagnetic colloidal particles with structure-specific substances or analytes that are to be identified can also be present in dried form, optionally in combination with other adjuvants which, e.g., facilitate drying or increase the stability of the dried product (e.g., as lyophilizates).

Finding of the analyte can be done with or without separation and washing steps. In carrying out measurements with separation steps between bound and unbound magnetic markers, all ferromagnetic or ferrimagnetic colloidal substances according to the invention can be used as magnetic labelings for magnet-relaxometric detection. In these cases, special requirements with regard to the Brownian relaxation times and the Néelian relaxation times no longer need be imposed.

Due to the binding identification based on physical mechanisms, non-specific measurement signals (matrix phenomena) can be largely ruled out. The specificity of the process thus depends only on the "true" specificity of the structure-specific substance (cross reactivity of antibodies, non-specific binding of ligands).

Due to the high sensitivity of the process according to the invention, it is easy to remain under the detection limits of binding assays that are otherwise commonly encountered.

As substances for magnetic labeling, all ferromagnetic or ferrimagnetic materials that can be dispersed colloidally in a medium that is suitable for magnetorelaxometric detection can be used. When using substances for magnetorelaxometric detection, which is carried out without separation steps between bound and unbound magnetic markers, the Néelian relaxation time of the magnetic labelings under the measurement conditions must be longer than the Brownian relaxation time of the magnetic markers. Especially suitable are all ferromagnetic or ferrimagnetic colloidal particles with Brownian relaxation times in aqueous media in the range of $10^{-8}$–$10^{-1}$ second and Néelian relaxation times of more than $10^{-8}$ second. To carry out measurements without separation steps, the viscosity of the dispersing medium used must be matched to the relaxation times of the ferromagnetic and ferrimagnetic particles and the measurement time since the suspension medium basically determines the time constant of Brownian relaxation.

Preferred are especially ferromagnetic or ferrimagnetic colloidal particles made of iron, iron oxides, barium ferrites, strontium ferrites, cobalt, nickel, nickel ferrites, cobalt ferrites, and chromium dioxide, whose Néelian relaxation time is longer than the Brownian relaxation time.

The use of magnetic labelings with narrowly distributed particle sizes and/or magnetic moments is generally advantageous. Separation of magnetic labelings into-fractions with a narrow distribution of particle sizes can be achieved by, e.g., chromatographic processes or by using special filtration processes (e.g., glass capillary systems or tangential filtration), by using molecular sieves, or by means of centrifuging. Magnetic labelings with moments that are as uniform as possible can be produced by, e.g., classification in a magnetic gradient field.

The ferromagnetic and ferrimagnetic substances can be stabilized with a shell that is made of oligomeric or polymeric carbohydrates, proteins, peptides, nucleotides, surfactants, other monomers, oligomers, or polymers and/or lipids.

The particle sizes of the ferromagnetic and ferrimagnetic substances are advantageously between 1 nm and 400 nm. Especially preferred are particle sizes between 1 nm and 100 nm.

According to the process, the magnet-relaxometric detection is carried out with measurement arrangements that first make it possible to magnetize the sample that is to be studied with the aid of a suitable magnetic field and then to measure the magnetic relaxation of the magnetic markers. A measurement arrangement for the magnet-relaxometric detection of analytes, as it was used in the examples, is depicted in FIG. 1. In contrast to all other already known processes (JP-235774 and WO 91/15243), in the measurement of the relaxation of magnetization in the process according to the invention, it is not static magnetization in the presence of the magnetizing field that is measured but rather its time change in the absence of the magnetizing field. Only thus are data on the binding state of the markers available. In addition, influencing of the measurement signal by diamagnetic or paramagnetic components or contaminants is thus avoided. Further, measurement sensitivity is increased decisively.

It is further possible to carry out the measurement of the frequency-dependent magnetization of the marker because of a suitable alternating magnetic field (determination of complex susceptibility as a function of frequency) with the aid of highly sensitive sensors, such as, for example, SQUIDs, in the presence of the field. In this case, use is made of the specific frequency dependence of the susceptibility of the magnetic marker, in contrast to the frequency dependence of the paramagnetic or diamagnetic components that can be determined separately. Also, this procedure differs from the process for determining the susceptibility of superparamagnetic substances that is proposed in WO 91/15243. In WO 91/15243, neither the frequency dependency of the susceptibility of the magnetic markers, nor a process for using this property is described.

Another aspect of the invention relates to processes that make it possible to detect the retention site and the extent of the specifically bound markers without being influenced by markers that circulate in the blood. In these processes, the use of radioactive substances, which in the past has been unavoidable in carrying out scintigraphy processes of the prior art, is avoided.

The processes according to the invention are based on the fact that the relaxation time differences between bound and unbound magnetic markers in liquids, as well as the change of the predominant relaxation mechanism by binding the magnetic markers to solid phases, can also be used for magnet-relaxometric detection of substances or structures in vivo. Such processes are also referred to below as immune magnetography or immunomagnetography.

The in vivo measurement of the spatial distribution of relaxing magnetic markers that are used in humans in the time range of the measurement can be carried out by two different measuring methods:

1. Production of as homogeneous a magnetic field as possible in advantageous volume, turning off the field and measuring the spatial distribution of the relaxing magnetic field with the aid of a multichannel sensor. Said sensor should enclose the measurement object as completely as possible. For the production of sufficient measurement information, repeated measurement with sequential rastering of the measurement object is also possible.

2. Sequential production of a local field that is limited in space, turning off the field and measuring the spatial distribution of the relaxing magnetic field with the aid of a single-channel sensor. The use of a multichannel sensor is also possible.

In the case of both methods, to obtain as many data as possible both the magnetization of the measurement object and the measuring of the resulting magnetic field in all three spatial directions are to be preferred.

The measurement can be described by a model, as is also used in the analysis of magnetic fields of bioelectric currents. The model of the magnetic dipole, multipole or multi-dipole is used there as a basis. The special parameters of the model, especially the sites of the dipoles or multipoles, are found by a suitable approximation process, which minimizes the deviations between measurement data and model parameters. These parameters provide information on the spatial distribution of the magnetized particles.

An analogous approach is known and proven for the analysis of magnetic fields of bioelectric currents.

As processes and compounds that are suitable for immune magnetography, all processes and substances that are cited for magnet-relaxometric detection can be used.

Especially suitable for carrying out immune magnetography are magnetic labelings, which are biodegradable and compatible. This is especially true of magnetic labelings, which consist of iron oxides.

To carry out binding-specific magnet-relaxometric detection in vivo, it is necessary that the Brownian relaxation times of the combinations, introduced in the human body, of ferrimagnetic or ferromagnetic substances with structure-specific substances at body temperature in bodily fluids be shorter than the Néelian relaxation times.

In immune magnetography, structure-specific substances are defined especially as all substances that bind specifically to structures of the human body to be identified. Especially suitable are antibodies, antibody fragments, agonists that bind specifically to receptors or their antagonists, specific peptides and proteins, receptors, enzymes, enzyme substrates, nucleotides, ribonucleic acids, deoxyribonucleic acids, carbohydrates, or lipoproteins. Among the agonists that bind to receptors, especially cytokines, lymphokines, or endothelins are suitable.

Well suited are all structure-specific substances that have a binding constant in the range of $10^5$–$10^{15}$ $(mol/l)^{-1}$. Especially suitable are all structure-specific substances that have a binding constant in the range of $10^7$–$10^{15}$ $(mol/l)^{-1}$.

The following examples are used for a more detailed explanation of the object of the invention, without intending that they be limited to this object.

EXAMPLES

Example 1

100 µg of a monoclonal antibody to collagen III, referred to below as anticollagen III, is dissolved in 500 µl of 0.1 M sodium bicarbonate solution. 1 ml of dextran-coated magnetite suspension (Meito Sangyo) with 1 mol of Fe/l and a particle size of about 40 nm is buffered via a Sephadex column (Pharmacia PD 10) with 0.1 M sodium bicarbonate. 0.5 ml of 10 mmol of sodium periodate solution is added to the suspension. The solution is allowed to stand in the dark for 2 hours. Then, it is eluted via a PD 10 with 0.1 M sodium bicarbonate solution. The anticollagen III solution is added to the suspension. The mixture is allowed to stand in the dark for 3 hours at 4° C. Then, 5 mg of $NaBH_4$ is added as a solid and briefly swirled. The mixture is allowed to stand in the dark for 8 hours at 4° C. Then, the magnetite-labeled anticollagen III (referred to below as mag-anticollagen III) is eluted via a PD 10 column with phosphate-buffered common salt solution (PBS below, pH 7.4).

A solution of 5 µg of collagen III in 200 µl of buffer (phosphate-buffered common salt solution (PBS)) is incubated in a polystyrene sampling vessel. Then, the liquid phase is discarded. The sampling vessel is flushed three times with phosphate-buffered common salt solution, containing 0.1% Tween® 20 (referred to as PBST below). 5 µl of mag-anticollagen III in 200 µl of PBST is added to the sample. It is incubated for 1 hour at room temperature. Then, the sample is magnetized in a magnetically shielded chamber in a field with an intensity of 2 mT 4 cm below the squid detector (see FIG. 1). 400 milliseconds after the magnetic field is turned off, the relaxation measurement is carried out over 100 seconds. In the sample, relaxation is identified from a diminishing field. The relaxation signal of the sample that contains collagen III is depicted in FIG. 2.

Example 2

Figure 3:
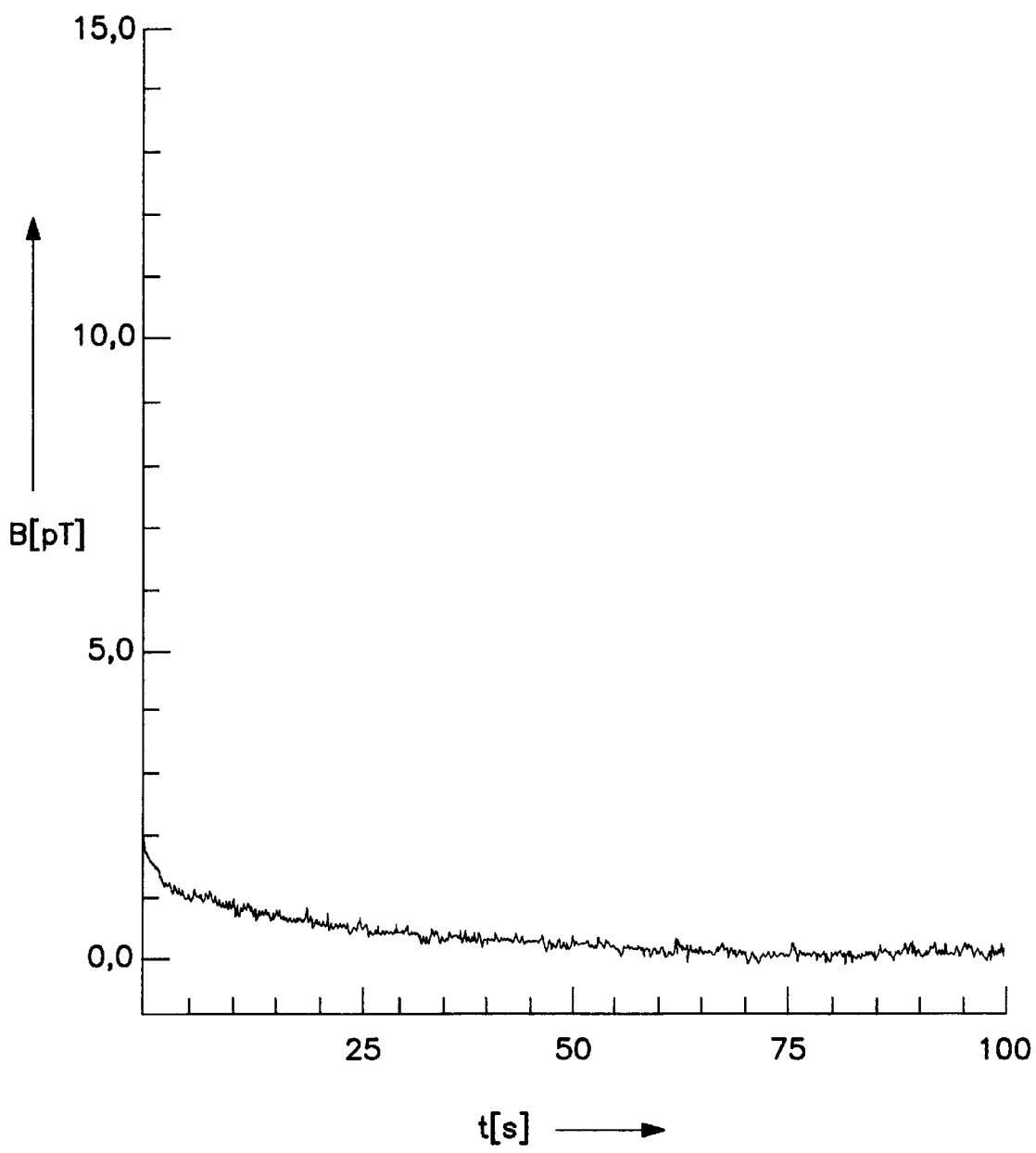

A solution of 5 µg of collagen V in 200 µl of PBS buffer of pH 7.4 is incubated in a polystyrene sampling vessel. Then, the liquid phase is discarded. The sampling vessel is flushed three times with PBST washing buffer of pH 7.4. 5 µl of mag-anticollagen III, produced according to Example 1, in 200 µl of PBST is added to the sample. It is incubated for 1 hour at room temperature. Then, the sample is magnetized in a magnetically shielded chamber in a field with an intensity of 2 mT 4 cm below the SQUID detector (see FIG. 1). After the magnetizing field is turned off, the sample is measured. 400 milliseconds after the magnetic field is turned off, the relaxation measurement is carried out over 100 seconds. In the sample that contains collagen V, no diminishing magnetic field can be detected within the limits of measurement reliability (see FIG. 3).

Example 3

100 µl of glutaric dialdehyde solution (3% in water) is added to a solution of 100 µg of collagen III in 1 ml of PBS. The solution is stirred for 24 hours at 4° C. and then centrifuged off. The pellet contains precipitated crosslinked collagen III. The crosslinked collagen III is suspended in 1 ml of PBS. (Sample 1). 100 µl of glutaric dialdehyde solution (3% in water) is added to a solution of 100 µg of collagen V in 1 ml of PBS. The solution is stirred for 24 hours at 4° C. and then centrifuged off. The pellet contains precipitated crosslinked collagen V. The crosslinked collagen V is suspended in 1 ml of PBS. (Sample 2). 5 µl each of mag-anticollagen III suspension of Example 1 is added to samples 1 and 2. It is incubated for 1 hour at 37° C. Then, both samples are magnetized in a shielded chamber in a magnetic field with an intensity of 2 mT via a SQUID detector. 400 milliseconds after the magnetizing field is turned off, the relaxation measurement is carried out. In the case of sample 1, a diminishing field is measured. In the case of sample 2, no diminishing field can be detected.

Example 4

From 10 ml of a 1.9 mg/ml collagen III solution in PBS (pH 7.4), 5 ml each of the following dilutions is produced:

10,000 ng/ml, 1,000 ng/ml, 100 ng/ml, 10 ng/ml, 1 ng/ml

Three times 1 ml each is pipetted from each dilution into polystyrene tubes (2.5 ml capacity). It is inhibited for 1 hour at 37° C. Then, the contents of the tubes are discarded. The tubes are washed three times with 1 ml of PBST each.

Figure 4:
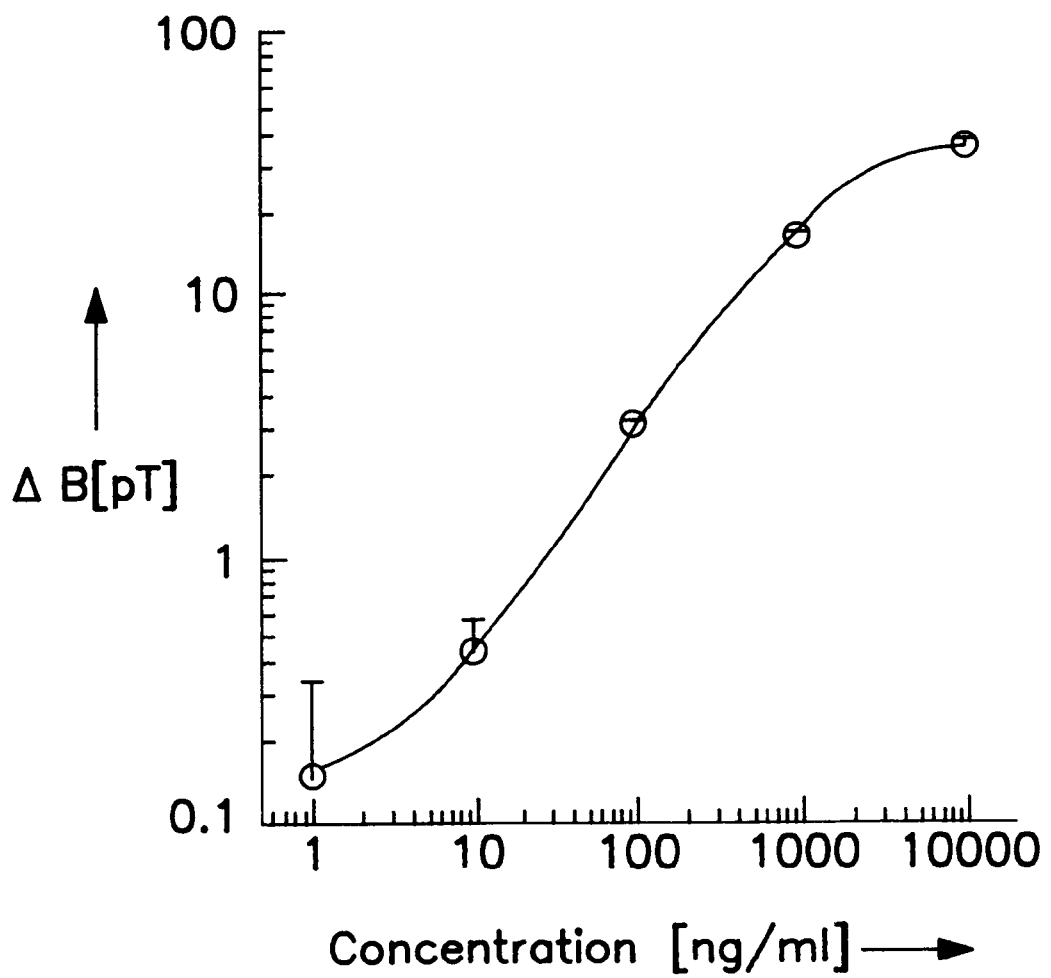
FIG. 4 represents a plot of concentration versus the differentiation in magnetic flux density of the samples.

1 ml of a 1:100 dilution of the magnetite-labeled antibody, produced according to Example 1, is added to each tube. The tubes are allowed to stand for 1 hour at room temperature. Then, the samples are magnetized (2 mT) with the measuring arrangement outlined in FIG. 1 and, after the magnetizing field is turned off, the relaxation is measured over 100 seconds. The evaluation of the differences of the measured magnetic flux densities B 200 milliseconds and 100 seconds after the magnetizing field is turned off is reproduced in FIG. 4 on the basis of the collagen concentration in the sample.

Example 5

100 µg of a monoclonal antibody to collagen III, referred to below as anticollagen III, is dissolved in 500 µl of 0.1 M sodium bicarbonate solution. 1 ml of dextran-coated magnetite suspension with 1 mol of Fe/l and a particle size of about 40 nm is buffered via a Sephadex column (Pharmacia PD 10) with 0.1 M sodium bicarbonate. 0.5 ml of 10 mmol of sodium periodate solution is added to the suspension. The solution is allowed to stand in the dark for 2 hours. Then, it is eluted via a PD 10 with 0.1 M of sodium bicarbonate solution. The anticollagen III solution is added to the suspension. The mixture is allowed to stand in the dark for 3 hours at 4° C. Then, 5 mg of NaBH$_4$ is added as a solid and briefly swirled. The mixture is allowed to stand in the dark for 8 hours at 4° C. Then, the magnetite-labeled anticollagen III (referred to below as mag-anticollagen III) is eluted via a PD 10 column with phosphate-buffered common salt solution (PBS, pH 7.4).

Figure 1:
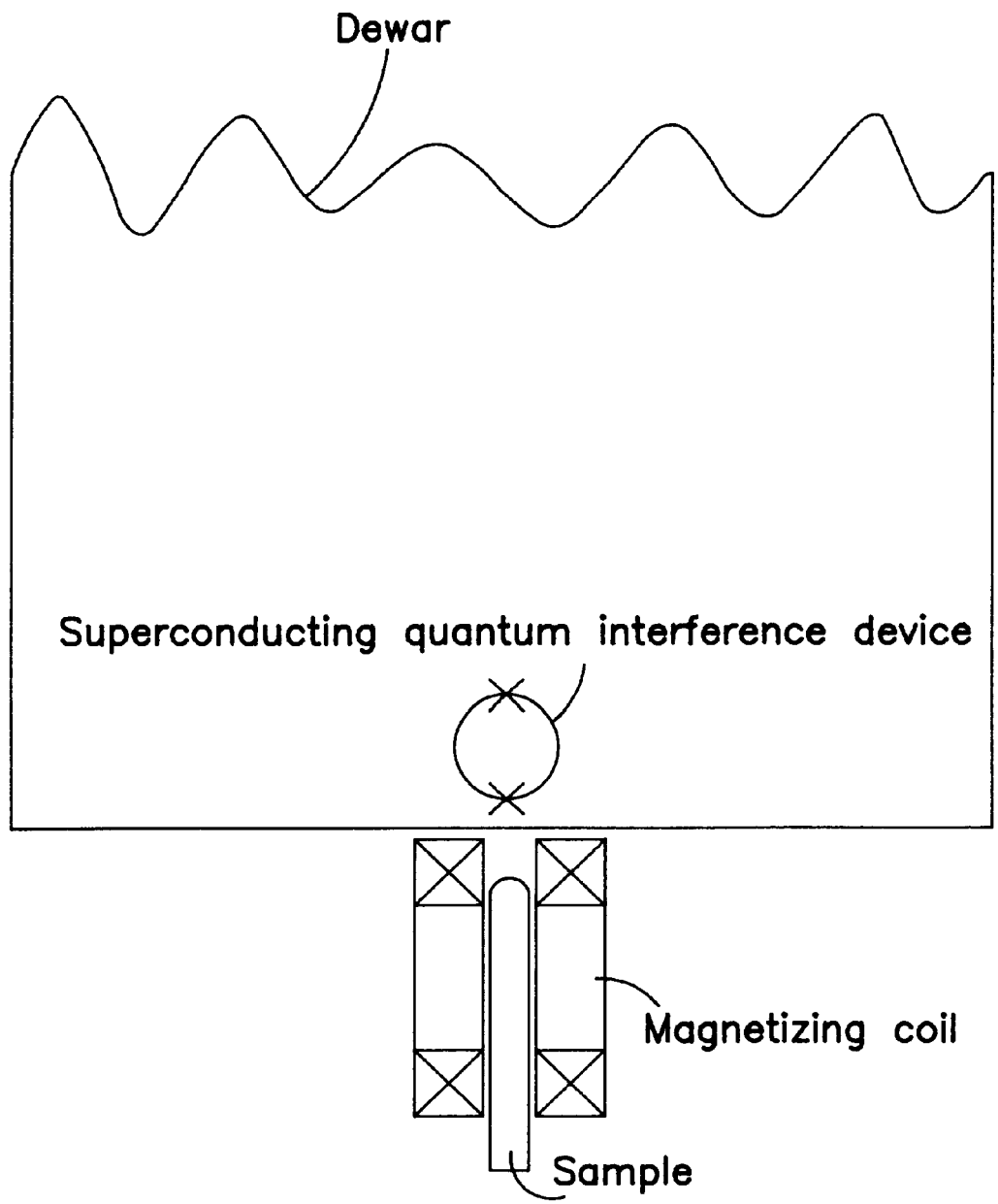
FIG. 1 represents a graph of magnetization of the sample.
Figure 2:
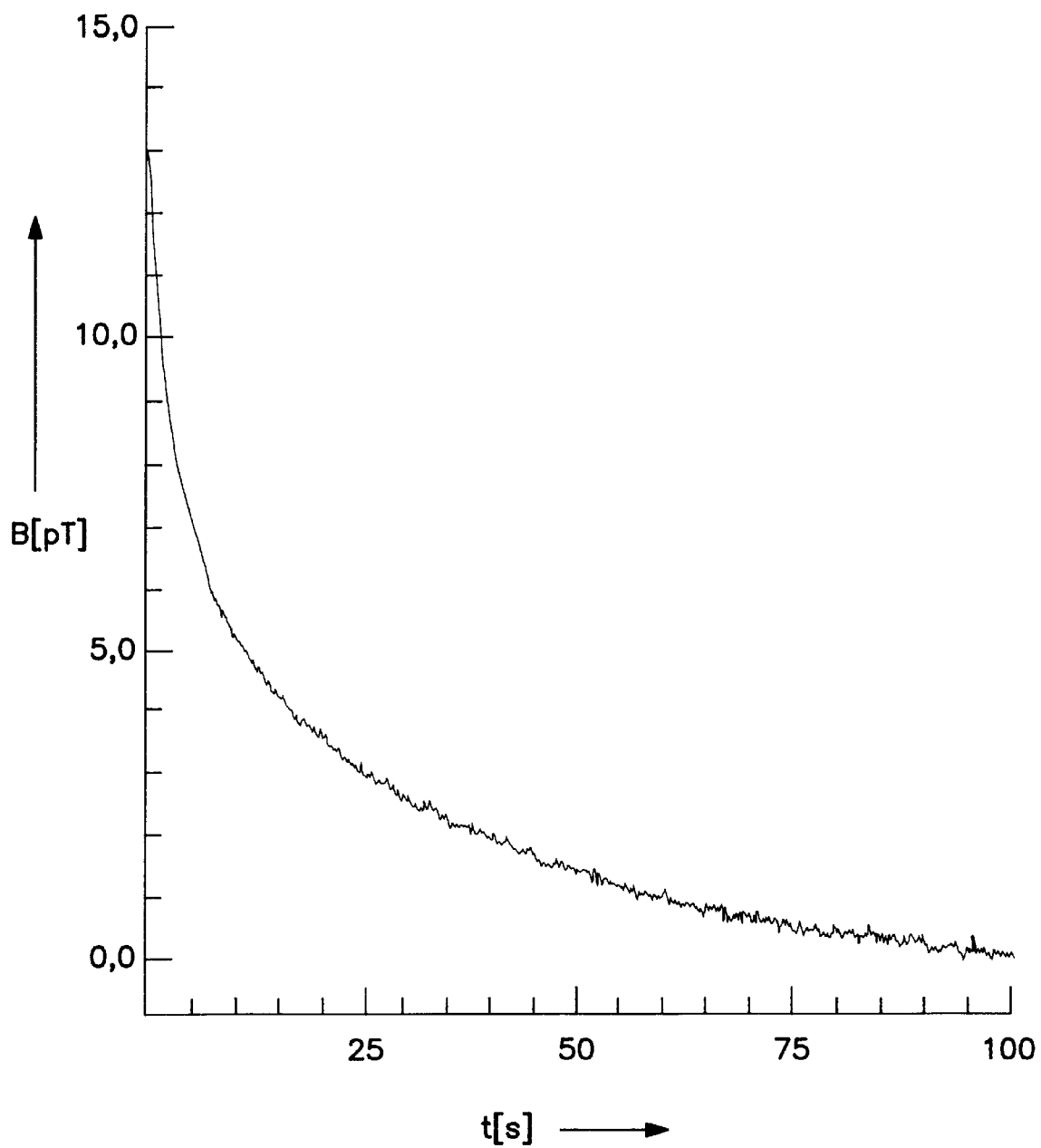
FIG. 2 and FIG. 3 represent graphs of relaxation of the sample.

20 μl each of the mag-anticollagen III suspension is diluted with 390 μl of phosphate-buffered common salt solution of pH 7.4, which in addition contains 0.1% PBST, and is filled in three sampling vessels made of polyacrylic acid, which in each case have a capacity of 500 μl. 100 μl of an aqueous solution of human serum albumin (1 mg of albumin/ml) is added to the first sampling vessel (sample 1). 100 μl of a solution of collagen V in PBST (1 μg of collagen V/ml) is added to the second sampling vessel (sample 2). 100 μl of a solution of collagen III in PBST (1 μg of collagen III/ml) is added to the third sampling vessel (sample 3). 200 seconds after the protein solutions are added, the samples are magnetized (2 mT) with the measuring arrangement outlined in FIG. 1, and 20 milliseconds after the magnetizing field is turned off, the magnetic relaxation is determined beginning with 1 second in each case. In samples 1 and 2, no diminishing magnetic field can be detected within the limits of measurement reliability. In sample 3, however, a diminishing magnetic field can be detected. After the sampling vessels are emptied and flushed three times with 500 μl of PBST each, the measurements are repeated. A diminishing magnetic field can now be detected in none of the sampling vessels within the limits of measurement reliability.

Example 6

100 μg of avidin is dissolved in 500 μl of 0.1 M sodium bicarbonate solution. 1 ml of dextran-coated magnetite suspension with 1 mol of Fe/l and a particle size of about 40 nm is buffered via a Sephadex column (Pharmacia PD 10) with 0.1 M sodium bicarbonate. 0.5 ml of 10 mmol of sodium periodate solution is added to the suspension. The solution is allowed to stand in the dark for 2 hours. Then, it is eluted via a PD 10 with 0.1 M sodium bicarbonate solution. The avidin solution is added to the suspension. The mixture is allowed to stand in the dark for 3 hours at 4° C. Then, 5 mg of NaBH$_4$ is added as a solid and briefly swirled. The mixture is allowed to stand in the dark for 8 hours at 4° C. Then, the magnetite-labeled avidin (referred to below as mag-avidin) is eluted via a PD 10 column with phosphate-buffered common salt solution (PBS, pH 7.4).

1 mg of bovine serum albumin is conjugated with biotin-N-hydroxysuccinimide (referred to below as biotin albumin) and diluted to a concentration of 1 μg/ml in PBS.

1 ml of the biotin-albumin dilution is incubated for 3 hours at room temperature in a polystyrene sampling vessel. Then, the liquid phase is discarded. The sampling vessel is flushed three times with phosphate-buffered common salt solution, containing 0.1% Tween® 20 (PBST). 5 μl of mag-avidin is added to the sample. It is incubated for 1 hour at room temperature. Then, the sample is magnetized in a magnetically shielded chamber in a field with an intensity of 2 mT 4 cm below the squid detector (see FIG. 1). 400 milliseconds after the magnetic field is turned off, the relaxation measurement is carried out over 100 seconds. In the sample, a diminishing magnetic field is measured.

1 ml of a dilution of bovine serum albumin in PBS (0.1 mg/ml) is incubated for 3 hours at room temperature in a polystyrene sampling vessel. Then, the liquid phase is discarded. The sampling vessel is flushed three times with phosphate-buffered common salt solution, containing 0.1% Tween® 20 (PBST). 5 μl of mag-avidin is added to the sample. It is incubated for 1 hour at room temperature. Then, the sample is magnetized in a magnetically shielded chamber in a field with an intensity of 2 mT 4 cm below the squid detector (see FIG. 1). 400 milliseconds after the magnetic field is turned off, the relaxation measurement is carried out over 100 seconds. In the sample, no diminishing magnetic field is measured within the limits of measurement reliability.

We claim:

1. A method for qualitative and/or quantitative detection of analytes in liquid phase or solid phase, comprising labeling the analytes with ferromagnetic colloidal particles or ferrimagnetic colloidal particles, and determining relaxation of magnetization of said labeled analytes as a qualitative or quantitative measurement of the analyte.

2. A process according to claim 1, comprising quantitatively detecting said analyte, wherein the ferromagnetic or ferrimagnetic colloidal particles have a Brownian relaxation under measurement conditions which is shorter than their Néelian relaxation.

3. A process according to claim 2, wherein the relaxation is determined by measuring complex susceptibility as a function of frequency.

4. A process according to claim 1, comprising (i) labeling structure-specific substances that bind the analytes with ferrimagnetic or ferromagnetic colloidal particles as magnetic markers and ii) introducing said labeled structure-specific substances in a liquid or immobilized sample to be measured, magnetizing the sample to be measured with the aid of a magnetic field that is applied from outside and, after turning the outside field off, measuring relaxation of magnetization of the magnetic markers with the aid of magnetic field sensors.

5. A process according to claim 1, comprising (i) labeling analytes with ferrimagnetic or ferromagnetic colloidal particles as magnetic markers and ii) introducing magnetically labeled analytes in a liquid or immobilized sample to be measured and containing substances that specifically bind the analytes, and the sample to be measured with the aid of a magnetic field that is applied from outside and, after turning off the field is turned off, measuring relaxation of magnetization of the magnetic markers with the aid of magnetic field sensors.

6. A process according to claim 1, comprising quantitative detection of solid-phase-bound analytes, by (i) labeling structure-specific substances that bind the analytes with ferrimagnetic or ferromagnetic colloidal particles that relax in the time range of the measurement as magnetic markers, whereby the ferrimagnetic or ferromagnetic colloidal particles have a Brownian relaxation shorter than a Néelian relaxation under measurement conditions and then ii) introducing magnetically labeled substances in an immobilized sample to be measured, and magnetizing with the aid of a magnetic field applied from outside and, after the field is turned off, measuring relaxation of magnetization of the magnetic markers with the aid of magnetic field sensors, and analyzing differences in relaxation behaviors of the magnetic markers bound with the analytes relative to the unbound magnetic markers.

7. A process according to claim 6, wherein substances that specifically bind the analytes are present in the sample.

8. A process according to claim 1, comprising quantitative detection of analytes present in liquid phase, by (i) labeling structure-specific substances that bind the analytes with ferrimagnetic or ferromagnetic colloidal particles having a Brownian relaxation time under measurement conditions shorter than Néelian relaxation as magnetic markers and ii) introducing the magnetically labeled substances in a sample to be measured, and magnetizing with the aid of a magnetic field that is applied from outside and, after turning the field off measuring relaxation of the magnetization of the magnetic markers with the aid of magnetic field sensors, and analyzing differences in relaxation behaviors of the magnetic markers bound with the analyte relative to the unbound magnetic markers.

9. A process according to claim 8, wherein substances specifically bind the analytes are added to the samples to be measured.

10. A process according to claim 1, comprising measurement of complex susceptibility as a function of frequency.

11. A process according to claim 4, wherein the structure-specific substances are antibodies, antibody fragments, biotin, substances that specifically bind biotin, agonists that bind specifically to receptors or their antagonists, peptides, proteins, enzymes, enzyme substrates, nucleotides, ribonucleic acids, deoxyribonucleic acids, carbohydrates, or lipoproteins.

12. A process according to claim 11, wherein the agonists that bind to receptors are cytokines, lymphokines, or endothelins.

13. A process according to claim 11, wherein the structure-specific substances have a binding constant of $10^5$–$10^{15}$ $(mol/l)^{-1}$.

14. A process according to claim 11, wherein the structure-specific substances have a binding constant of $10^7$–$10^{15}$ $(mol/l)^{-1}$.

15. A process according to claim 1, wherein magnetization is measured with magnetic field sensors, which are superconducting quantum interference devices (SQUIDs), induction coils, flux gate magnetometers, giant magnetoresistance sensors, or magnetoresistive converters.

16. A process according to claim 1, comprising determining relaxation of two or more different analytes in a sample.

17. A process according to claim 16, wherein two or more ferromagnetic or ferrimagnetic colloidal particles with discriminatable Brownian or Néelian relaxation times are used.

18. A process according to claim 1, wherein the ferromagnetic and ferrimagnetic colloidal particles have a particle size of 1 to 400 nm.

19. A process according to claim 1, wherein the ferromagnetic and ferrimagnetic colloidal particles have a particle size of 1 to 100 nm.

20. A process according to claim 1, wherein the ferromagnetic and ferrimagnetic colloidal particles are stabilized with a shell made of oligomeric or polymeric carbohydrates, proteins, peptides, nucleotides, and/or lipids.

21. A process according to claim 5, wherein the substances which bind the analytes are antibodies, antibody fragments, biotin, substances that specifically bind biotin, agonists that bind specifically to receptors or their antagonists, peptides proteins, enzymes, enzyme substrates, nucleotides, ribonucleic acids, deoxyribonucleic acids, carbohydrates, or lipoproteins.

22. A process according to claim 6, wherein the structure-specific substances are antibodies, antibody fragments, biotin, substances that specifically bind biotin, agonists that bind specifically to receptors or their antagonists, peptides, proteins, enzymes, enzyme substrates, nucleotides, ribonucleic acids, deoxyribonucleic acids, carbohydrates, or lipoproteins.

23. A process according to claim 8, wherein the structure-specific substances are antibodies, antibody fragments, biotin, substances that specifically bind biotin, agonists that bind specifically to receptors or their antagonists, peptides, proteins, enzymes, enzyme substrates, nucleotides, ribonucleic acids, deoxyribonucleic acids, carbohydrates, or lipoproteins.

* * * * *